United States Patent
Al Kawai et al.

(10) Patent No.: US 11,649,721 B2
(45) Date of Patent: May 16, 2023

(54) HYDROCARBON EVALUATION SYSTEMS

(71) Applicant: Saudi Arabian Oil Company, Dhahran (SA)

(72) Inventors: Wisam Al Kawai, Qatif (SA); Abrar Alabbad, Al-Jish (SA)

(73) Assignee: Saudi Arabian Oil Company, Dhahran (SA)

( * ) Notice: Subject to any disclaimer, the term of this patent is extended or adjusted under 35 U.S.C. 154(b) by 360 days.

(21) Appl. No.: 16/909,389

(22) Filed: Jun. 23, 2020

(65) Prior Publication Data

US 2021/0396134 A1 Dec. 23, 2021

(51) Int. Cl.
*E21B 47/13* (2012.01)
*E21B 47/135* (2012.01)
*E21B 49/00* (2006.01)
*E21B 49/08* (2006.01)
*G01N 21/17* (2006.01)
*G01V 1/50* (2006.01)

(52) U.S. Cl.
CPC .......... *E21B 47/135* (2020.05); *E21B 49/003* (2013.01); *E21B 49/087* (2013.01); *G01N 21/17* (2013.01); *G01V 1/50* (2013.01); *G01N 2021/177* (2013.01); *G01V 2210/1299* (2013.01)

(58) Field of Classification Search
CPC .... E21B 47/135; E21B 49/003; E21B 49/087; G01N 21/17; G01N 2021/177; G01V 1/50; G01V 2210/1299
See application file for complete search history.

(56) References Cited

U.S. PATENT DOCUMENTS 3,551,678 A * 12/1970 Mitchell ................ G01N 21/86
162/263
4,920,792 A 5/1990 Difoggio
(Continued)

FOREIGN PATENT DOCUMENTS

GB 2217838 11/1989
WO 2011077271 6/2011

OTHER PUBLICATIONS

Chen et al., "The Detection and Prediction for Oil Spill on the Sea Based on the Infrared Images," Infrared Physics and Technology, Jul. 2016, 77: 391-404.
(Continued)

*Primary Examiner* — Elias Desta
(74) *Attorney, Agent, or Firm* — Fish & Richardson P.C.

(57) ABSTRACT

Systems and methods for evaluating hydrocarbon properties. At least one of the systems includes: a drilling machine configured to drill a borehole; a plurality of infrared cameras configured to capture infrared image data representing a plurality of infrared images of at least one core sample extracted from the borehole; a computer-readable memory comprising computer-executable instructions; and at least one processor configured to execute the computer-executable instructions, in which when the at least one processor is executing the computer-executable instructions, the at least one processor is configured to carry out operations including: receiving the infrared image data captured by the plurality of infrared cameras; determining, based on the infrared image data, at least one hydrocarbon weight value of the at least one core sample.

15 Claims, 4 Drawing Sheets

(56) References Cited

U.S. PATENT DOCUMENTS

| | | | |
|---|---|---|---|
| 5,473,162 A * | 12/1995 | Busch | G01N 21/72 250/339.08 |
| 6,281,498 B1 * | 8/2001 | Fellows | G01N 21/3554 250/339.01 |
| 6,420,869 B1 | 7/2002 | Difoggio | |
| 6,995,360 B2 | 2/2006 | Jones et al. | |
| 7,173,239 B2 | 2/2007 | Difoggio | |
| 7,196,786 B2 | 3/2007 | Difoggio | |
| 7,362,422 B2 | 4/2008 | Difoggio et al. | |
| 7,566,855 B2 * | 7/2009 | Olsen | H01L 27/14621 250/208.1 |
| 7,653,509 B2 * | 1/2010 | Bagwell | G06K 9/6277 702/19 |
| 7,705,982 B2 | 4/2010 | Triana et al. | |
| 8,332,162 B2 | 12/2012 | Abahri | |
| 9,778,240 B2 | 10/2017 | Koseoglu et al. | |
| 9,797,822 B2 | 10/2017 | Little, III et al. | |
| 2010/0207018 A1 | 8/2010 | Djordjevic et al. | |
| 2015/0106031 A1 | 4/2015 | Koseoglu et al. | |
| 2015/0139273 A1 | 5/2015 | Bagley et al. | |
| 2015/0176407 A1 | 6/2015 | Indo et al. | |
| 2016/0187509 A1 | 6/2016 | Boot et al. | |
| 2019/0094137 A1 | 3/2019 | Little, III et al. | |

OTHER PUBLICATIONS

Pabon et al., "Crude Oil Spectral Signatures and Empirical Models to Derive API Gravity," Fuel, 2019, 237: 1119-1131.

PCT International Search Report and Written Opinion in International Appln. No. PCT/US2021/038640, dated Oct. 11, 2021, 18 pages.

* cited by examiner

HYDROCARBON EVALUATION SYSTEMS

TECHNICAL FIELD

The present disclosure generally relates to hydrocarbon exploration

BACKGROUND

Hydrocarbon exploration (for example, oil and gas exploration) can include searching for deposits of hydrocarbons, particularly petroleum and natural gas, in the Earth using petroleum geology. Visible surface features such as oil seeps, natural gas seeps, pockmarks (underwater craters caused by escaping gas) can provide evidence of hydrocarbon generation (be it shallow or deep in the Earth). However, some exploration depends on highly sophisticated technology to detect and determine the extent of these deposits using exploration geophysics. Areas thought to contain hydrocarbons can be initially subjected to a gravity survey, magnetic survey, and passive seismic or regional seismic reflection surveys to detect large-scale features of the subsurface geology. Features of interest (known as leads) may be subjected to more detailed seismic surveys, which can work on the principle of the time it takes for reflected sound waves to travel through matter (rock) of varying densities and using the process of depth conversion to create a profile of the substructure. When a prospect has been identified and evaluated, and passes some selection criteria, an exploration well can be drilled in an attempt to conclusively determine the presence or absence of oil or gas. Hydrocarbon exploration is often an expensive, high-risk operation.

In geology, sedimentary facies are bodies of sediment that are recognizably distinct from adjacent sediments that resulted from different depositional environments. Generally, geologists can distinguish facies by aspects of the rock or sediment being studied. Seismic facies are groups of seismic reflections whose parameters (such as amplitude, continuity, reflection geometry, and frequency) differ from those of adjacent groups. Seismic facies analysis, a subdivision of seismic stratigraphy, plays an important role in hydrocarbon exploration and is one key step in the interpretation of seismic data for reservoir characterization. The seismic facies in a given geological area can provide useful information, particularly about the types of sedimentary deposits and the anticipated lithology.

The American Petroleum Institute gravity (API gravity), is a measure of how heavy or light a petroleum liquid is compared to water. If the liquid's API gravity is greater than 10, it is lighter and floats on water. If it is less than 10, the liquid is heavier and sinks. API gravity can, therefore, be defined as an inverse measure of a petroleum liquid's density relative to that of water (also known as specific gravity). It can be used to compare densities of petroleum liquids. For example, if one petroleum liquid is less dense than another, it has a greater API gravity. Although API gravity is mathematically a dimensionless quantity (see the formula below), it is referred to as being in "degrees." API gravity can be graduated in degrees on a hydrometer instrument. API gravity values of many petroleum liquids fall between 10 and 70 degrees.

Generally, oil with an API gravity between 40 and 45 degree can command the highest prices. In oil with an API above 45 degrees, the molecular chains can become shorter and less valuable to refineries. Crude oil can be classified as light, medium, or heavy according to its measured API gravity. Light crude oil can have an API gravity higher than 31.1 degrees, medium oil can have an API gravity between 22.3 and 31.1 degrees, heavy crude oil can have an API gravity below 22.3 degrees, and extra heavy oil can have an API gravity below 10.0 degrees.

SUMMARY

Implementations of the present disclosure provide systems and methods for distinguishing variations in petroleum API gravity that can be used before drilling a conventional exploration well. In some implementations, the systems and methods use images of core samples having hydrocarbon stains captured at different wavelengths across the infrared spectrum to distinguish variations in the petroleum API. In some implementations, one or more machine learning techniques are used to facilitate the distinguishing of variations in the petroleum API.

In an aspect, a system for evaluating hydrocarbon properties is provided. The system includes a drilling machine configured to drill a borehole. The system includes a plurality of infrared cameras configured to capture infrared image data representing a plurality of infrared images of at least one core sample extracted from the borehole. The system includes a computer-readable memory comprising computer-executable instructions. The system includes at least one processor configured to execute the computer-executable instructions, in which when the at least one processor is executing the computer-executable instructions, the at least one processor is configured to carry out one or more operations. The one or more operations include receiving the infrared image data captured by the plurality of infrared cameras. The one or more operations include determining, based on the infrared image data, at least one hydrocarbon weight value of the at least one core sample.

Determining at least one hydrocarbon weight property can include executing at least one machine learning model trained to predict an American Petroleum Institute (API) gravity value based on infrared intensity values of the infrared image data. Determining at least one hydrocarbon weight can be further based on a plurality of predetermined probability density functions defined by a plurality of measured intensity values. Determining at least one hydrocarbon weight property can include executing at least one machine learning model trained to predict a probability of a plurality of API gravity values based on infrared intensity values of the infrared image data.

The plurality of IR cameras can include: at least one short-wavelength IR camera configured to capture infrared image data at wavelengths between 1400 nanometers (nm) and 3000 nm; at least one mid-wavelength IR camera configured to capture infrared image data at wavelengths between 3000 nm and 8000 nm; and at least one long-wavelength IR camera configured to capture infrared image data at wavelengths between 8000 nm and 15000 nm. The drilling machine can include a portable drilling machine configured to drill a maximum borehole depth of 3000 meters (m). The plurality of IR cameras can be configured to capture infrared data at wavelengths between 1400 nm and 15000 nm.

These and other aspects, features, and implementations can be expressed as methods, apparatus, systems, components, program products, non-transitory computer storage mediums, means or steps for performing a function, and in other ways, and will become apparent from the following descriptions, including the claims.

Implementations of the present disclosure include one or more of the following advantages. Unlike conventional techniques: API gravity of oil can be determined at the borehole without having to extract liquid well samples of oil; API gravity information can be obtained without drilling conventional exploration wells; assessment of the quality of API gravity determination can be performed, probability density functions of APIs can be defined, and, for a given oil stained core sample, probabilities for two or more APIs of the oil stain can be determined.

The details of one or more implementations of these systems and methods are set forth in the accompanying drawings and the description to be presented. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

Hydrocarbons (for example, oils) of different density and viscosity have different American Petroleum Institute gravity (API gravity). Determination of API gravity of oil at the borehole can have important applications for recovery of oil from the subsurface formation, along with other applications for oil production. For example, spatial delineation of accumulations of heavy oils can be important in properly applying enhanced recovery methods. Enhanced recovery methods can be important for recovery of heavy oil because of the high viscosity of heavy oil. Oil API can be measured in the field using a hydrometer after obtaining well samples of oil. Intensities of fluorescence under ultraviolet light can also be used to estimate oil API gravity from formation samples. Some of these methods may have limitations on providing estimates of oil API prior to drilling a conventional well. These limitations can cause uncertainty about oil and it's API, which can translate into an economic risk because such information can be important in making informed decision to drill a conventional well. These limitations can cause difficulty in applying proper recovery methods in newly drilled areas because of lack of information on oil and its API.

Knowing information such as spatial delineation of heavy oils prior to exploring of oil can improve the economic returns from oil exploration. Such input can reduce the risk in drilling decisions and also help optimizing the recovery methods at the zones of heavy oil.

Implementations of the present disclosure describes systems and methods for distinguishing variations in petroleum API gravity that can be used before drilling a conventional exploration well. In some implementations, the systems and methods use a plurality of infrared (IR) cameras, each using a different band of IR wavelength, to capture images of core samples extracted using a relatively small borehole (when compared to conventionally sized boreholes). The core samples can include hydrocarbon (for example, oil) stains. In some implementations, the systems and methods use the captured images of core samples having hydrocarbon stains to assess the API of the hydrocarbon stains on the core sample. In some implementations, one or more machine learning techniques are used to facilitate the API assessment. In some implementations, the core samples are extracted using a portable drilling machine that is capable of drilling to a depth of 3000 meters (m), which can be deep enough extract usable core samples from shallow hydrocarbon reservoirs.

Figure 1:
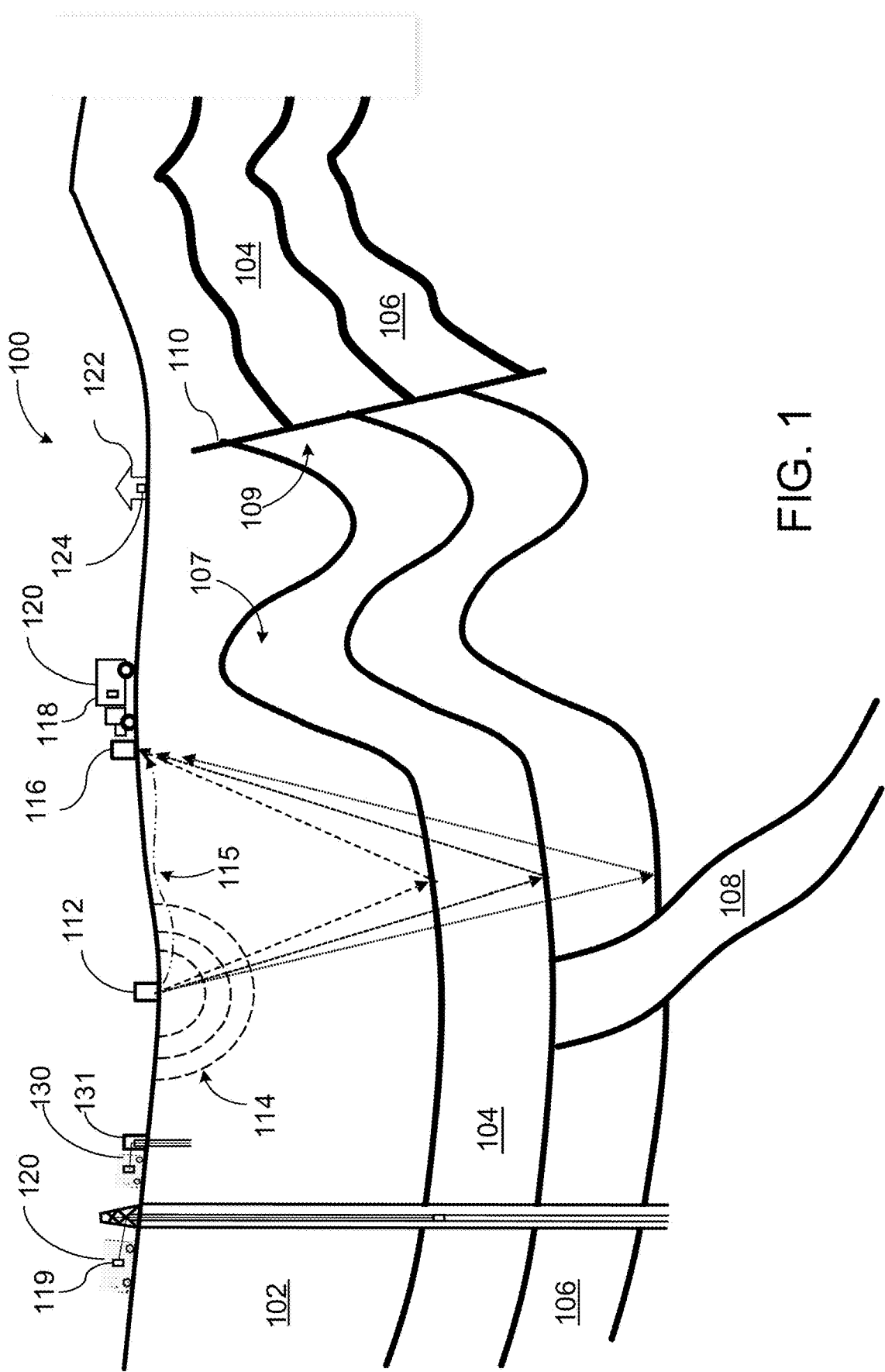
FIG. 1 is a schematic view of a seismic survey being performed to map subterranean features such as facies and faults.

FIG. 1 is a schematic view of a seismic survey being performed to map subterranean features such as facies and faults in a subterranean formation 100. The subterranean formation 100 includes a layer of impermeable cap rock 102 at the surface. Facies underlying the impermeable cap rocks 102 include a sandstone layer 104, a limestone layer 106, and a sand layer 108. A fault line 110 extends across the sandstone layer 104 and the limestone layer 106.

Oil and gas tend to rise through permeable reservoir rock until further upward migration is blocked, for example, by the layer of impermeable cap rock 102. Seismic surveys attempt to identify locations where interaction between layers of the subterranean formation 100 are likely to trap oil and gas by limiting this upward migration. For example, FIG. 1 shows an anticline trap 107, where the layer of impermeable cap rock 102 has an upward convex configuration, and a fault trap 109, where the fault line 110 might allow oil and gas to flow in with clay material between the walls traps the petroleum. Other traps include salt domes and stratigraphic traps.

A seismic source 112 (for example, a seismic vibrator or an explosion) generates seismic waves that propagate in the earth. Although illustrated as a single component in FIG. 1, the source or sources 112 are typically a line or an array of sources 112. The generated seismic waves include seismic body waves 114 that travel into the ground and seismic surface waves 115 travel along the ground surface and diminish as they get further from the surface.

The velocity of these seismic waves depends properties, for example, density, porosity, and fluid content of the medium through which the seismic waves are traveling. Different geologic bodies or layers in the earth are distinguishable because the layers have different properties and, thus, different characteristic seismic velocities. For example, in the subterranean formation 100, the velocity of seismic waves traveling through the subterranean formation 100 will be different in the sandstone layer 104, the limestone layer 106, and the sand layer 108. As the seismic body waves 114 contact interfaces between geologic bodies or layers that have different velocities, each interface reflects some of the energy of the seismic wave and refracts some of the energy of the seismic wave. Such interfaces are sometimes referred to as horizons.

The seismic body waves 114 are received by a sensor or sensors 116. Although illustrated as a single component in FIG. 1, the sensor or sensors 116 are typically a line or an array of sensors 116 that generate an output signal in response to received seismic waves including waves reflected by the horizons in the subterranean formation 100. The sensors 116 can be geophone-receivers that produce electrical output signals transmitted as input data, for example, to a computer 118 on a seismic control truck 120.

Based on the input data, the computer 118 may generate a seismic data output, for example, a seismic two-way response time plot.

The seismic surface waves 115 travel more slowly than seismic body waves 114. Analysis of the time it takes seismic surface waves 115 to travel from source to sensor can provide information about near surface features.

A control center 122 can be operatively coupled to the seismic control truck 120 and other data acquisition and wellsite systems. The control center 122 may have computer facilities for receiving, storing, processing, and analyzing data from the seismic control truck 120 and other data acquisition and wellsite systems. For example, computer systems 124 in the control center 122 can be configured to analyze, model, control, optimize, or perform management tasks of field operations associated with development and production of resources such as oil and gas from the subterranean formation 100. Alternatively, the computer systems 124 can be located in a different location than the control center 122. Some computer systems are provided with functionality for manipulating and analyzing the data, such as performing seismic interpretation or borehole resistivity image log interpretation to identify geological surfaces in the subterranean formation or performing simulation, planning, and optimization of production operations of the wellsite systems.

In some implementations, results generated by the computer systems 124 may be displayed for user viewing using local or remote monitors or other display units. One approach to analyzing seismic data is to associate the data with portions of a seismic cube representing represent the subterranean formation 100. The seismic cube can also be display results of the analysis of the seismic data associated with the seismic survey.

Seismic surveys can be computationally and resource intensive, and establishing conventional wells can be very costly in terms of money, time, and resources. Therefore, it may be beneficial to obtain information related to the quality and type of oil before conducting a seismic survey and establishing a conventional well. The systems and method described in this specification can facilitate decisions as to whether to perform the seismic survey, whether to establish the conventional well, and the type of extraction techniques the conventional well will need to perform according to the type of oil to be extracted. In the illustrated implementation, a portable well truck 130 is used to place a portable drilling system 131 (for example, a portable drilling rig). The portable drilling system 131 is used to drill a relatively small borehole (relative to a conventional well) to obtain core samples, in which some of the core samples can be stained with oil. The core samples can be analyzed using the methods and systems discussed later in this specification to determine an API value of the oil at the borehole location. The information regarding the API value can be used to inform drilling decisions and whether to apply methods for enhancing oil recovery of heavy hydrocarbons, among others. Although, in the illustrated implementation, the portable drilling system 131 is used to drill a small borehole proximate to the illustrated location of the conventional well, in some implementations, the portable drilling system 131 drills a borehole at the location that the conventional well will be established, if it is decided to establish the conventional well.

Figure 2:
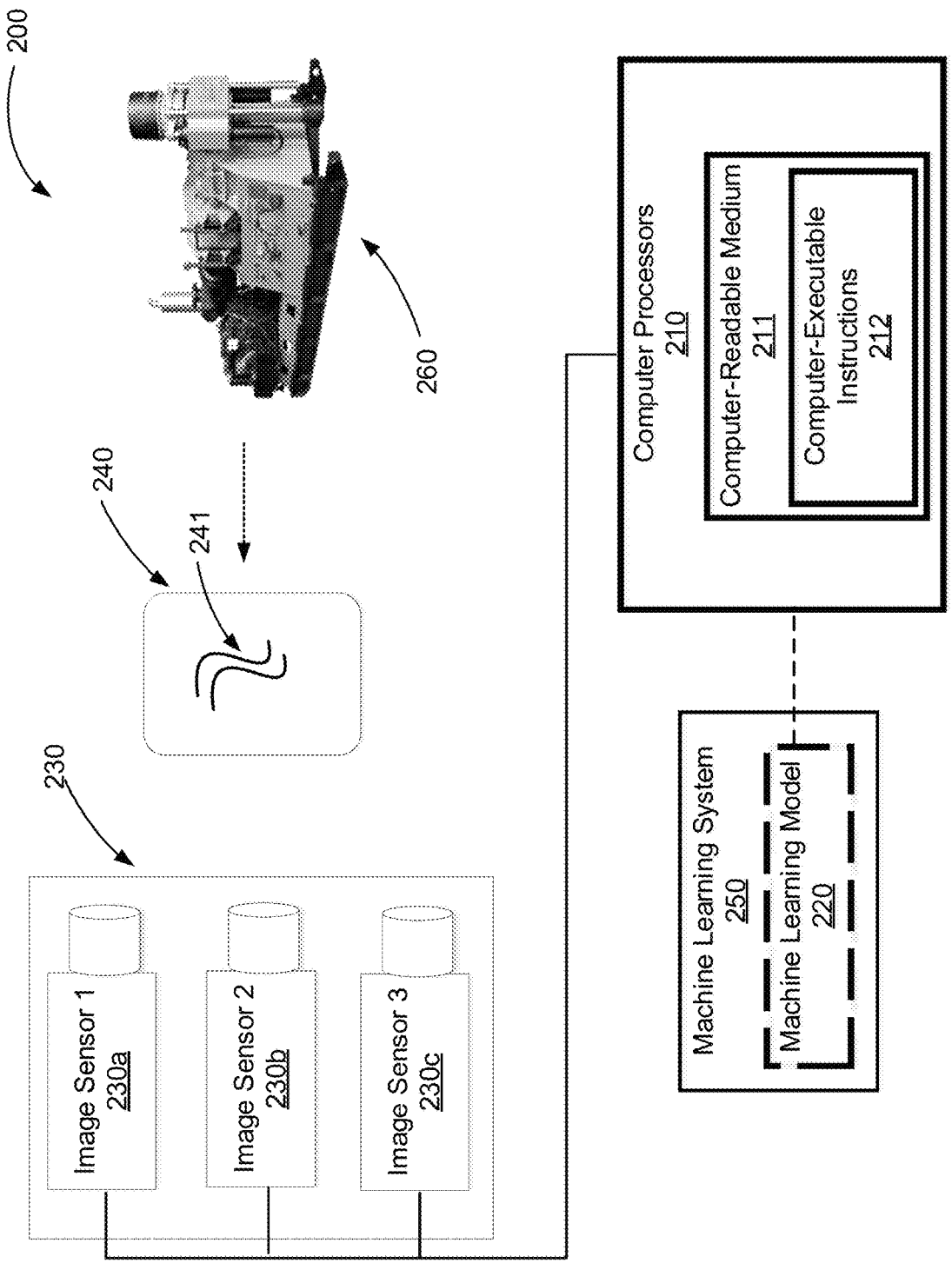
FIG. 2 is a block diagram illustrating an example system for evaluating hydrocarbon properties.

FIG. 2 is a block diagram illustrating an example system 200 for evaluating hydrocarbon properties. The system 200 includes one or more computer processors 210, a plurality if imaging sensors 230, a machine learning system 250, and a drilling system 260.

In the illustrated implementation, the drilling system 260 includes a portable drilling rig configured to drill boreholes up to 3000 meters (m) in depth and having a diameter up to 325 millimeters (mm). The drilling system include an alternating current (AC) motor and a drag bit, which describes a drill bit that is usually designed for use in earth formations such as sand, clay, soft rock, and so forth. The drilling system 260 includes a drill rod with a diameter of 89 to 102 mm and operates with a working pressure of up to 20 Megapascals (MPa). The drilling system 260 can facilitate extraction of rock samples 240, which can exhibit oil stains 241. Although certain specification and components of the illustrated drilling system 260 are described, some implementations include different drilling systems including combinations of different components and specifications.

The plurality of image sensors 230 include a first image sensor 230a, a second image second 230b, and a third image sensor 230c. Each of the plurality of image sensors 230 include an infrared camera configured to generate an image using infrared radiation. Although the plurality of image sensors 230 is described as having three IR cameras, in some implementations, the plurality of image sensors 230 includes more or fewer IR cameras. The first image sensor 230a includes a short-wavelength IR camera sensitive to infrared light having wavelengths between 1400 nanometers (nm) and 3000 nm. The second image sensor 230b includes a mid-wavelength IR camera that is sensitive to light having wavelengths between 3000 nm and 8000 nm. The third image sensor 230c includes a long-wavelength IR camera that is sensitive to light having wavelengths between 8000 nm to 15000 nm. Although each of the plurality of image sensors 230 is described as being sensitive to particular wavelength band, in some implementations, other wavelength bands are used. Each of the plurality of image sensors 230 are configured to capture image data representing an IR image of the rock sample 240 and the oil stains 241. The image data includes an IR spectral response that describes the intensity of IR light within the prescribed wavelengths of each image sensor 230. As indicated earlier, and will be described in more detail later, the intensity values of the spectral response can be used to determine an API gravity value of the oil 241.

The computer processors 210 include computer-readable memory 211 and computer readable instructions 212. The machine learning system 250 includes a machine learning model 220. The machine learning model 220 can be separate from or integrated with the computer processors 210.

The computer-readable medium 211 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable medium 211 includes code-segment having executable instructions.

In some implementations, the computer processors 210 include a general purpose processor. In some implementations, the computer processors 210 include a central processing unit (CPU). In some implementations, the computer processors 210 include at least one application specific integrated circuit (ASIC). The computer processors 210 can also include general purpose programmable microprocessors, graphic processing units, special-purpose programmable microprocessors, digital signal processors (DSPs), programmable logic arrays (PLAs), field programmable gate arrays (FPGA), special purpose electronic circuits, among others, or a combination of them. The computer processors 210 are configured to execute program code such as the computer-executable instructions 212 and configured to execute executable logic that includes the machine learning model 220.

The computer processors 210 are configured to receive the captured infrared image data. The image data can be obtained through any of various techniques, such as wireless communications with databases, optical fiber communications, USB, CD-ROM, directly from the plurality of image sensors 230, and so on.

The machine learning system 250 is capable of applying machine learning techniques to train the machine learning model 220. As part of the training of the machine learning model 220, the machine learning system 250 forms a training set of input data by identifying a positive training set of input data items that have been determined to have the property in question, and, in some implementations, forms a negative training set of input data items that lack the property in question.

The machine learning system 250 extracts feature values from the input data of the training set, the features being variables deemed potentially relevant to whether or not the input data items have the associated property or properties. An ordered list of the features for the input data is referred to as the feature vector for the input data in this specification. In some implementations, the machine learning system 250 applies dimensionality reduction (e.g., via linear discriminant analysis (LDA), principle component analysis (PCA), or the like) to reduce the amount of data in the feature vectors for the input data to a smaller, more representative set of data.

In some implementations, the machine learning system 250 uses supervised machine learning to train the machine learning models 220 with the feature vectors of the positive training set and the negative training set serving as the inputs. Different machine learning techniques—such as linear support vector machine (linear SVM), boosting for decision algorithms (e.g., AdaBoost), neural networks, logistic regression, naïve Bayes, memory-based learning, random forests, bagged trees, decision trees, boosted trees, or boosted stumps—may be used in different implementations. The machine learning model 220, when applied to the feature vector extracted from the input data item, outputs an indication of whether the input data item has the property in question, such as a Boolean yes/no estimate, or a scalar value representing a probability.

In some implementations, a validation set is formed of additional input data, other than those in the training sets, which have already been determined to have or to lack the property in question. The machine learning system 250 applies the trained machine learning model 220 to the data of the validation set to quantify the accuracy of the machine learning model 220. Common metrics applied in accuracy measurement include: Precision=TP/(TP+FP) and Recall=TP/(TP+FN), where precision is how many the machine learning model correctly predicted (TP or true positives) out of the total it predicted (TP+FP or false positives), and recall is how many the machine learning model correctly predicted (TP) out of the total number of input data items that did have the property in question (TP+FN or false negatives). The F score (F-score=2*PR/(P+R)) unifies precision and recall into a single measure. In one implementation, the machine learning module iteratively re-trains the machine learning model until the occurrence of a stopping condition, such as the accuracy measurement indication that the model is sufficiently accurate, or a number of training rounds having taken place.

The trained machine learning model 220 is capable of processing the IR image data to predict an API value of the oil corresponding to the oil stains 241 based on the IR intensity values of the IR image data. For example, as indicated previously, the oil of the oil stains 241 can produce different spectral responses (for example, in terms of intensity values) at different wavelengths based on the API gravity of the oil. In some implementations, the machine learning model 220 can obtain these spectral responses from the IR image data and compare them with predefined probability density functions corresponding to intensity values at different IR wavelengths for different API values. In some implementations, the machine learning model 220 is capable of determining, for each oil stain 241, the probability of several API values (for example, the probability that the oil stain 241 has a first API value and a probability that the oil stain 231 has a second API value) using the predefined probability density functions.

One or more techniques can be used to generate the predefined probability density functions. In the illustrated implementation, a collection of core samples with oil stains having known API measurements (for example, using one or more traditional API measurement techniques) are obtained to generate a Bayesian classification training set. IR cameras of different wavelength bands are used to obtain images of the oil stained core samples. Using the obtained images, intensity values across different wavelengths of IR light are mapped to the different API values. A single API value can have a distribution of intensity values at a certain wavelength of IR. Therefore, probability density functions of intensity values at a certain IR wavelengths can be defined. The compilation of various probability density functions for different API values can be used to establish a database or training set for future classifications of API values based on spectral responses corresponding to future images.

Figure 3:
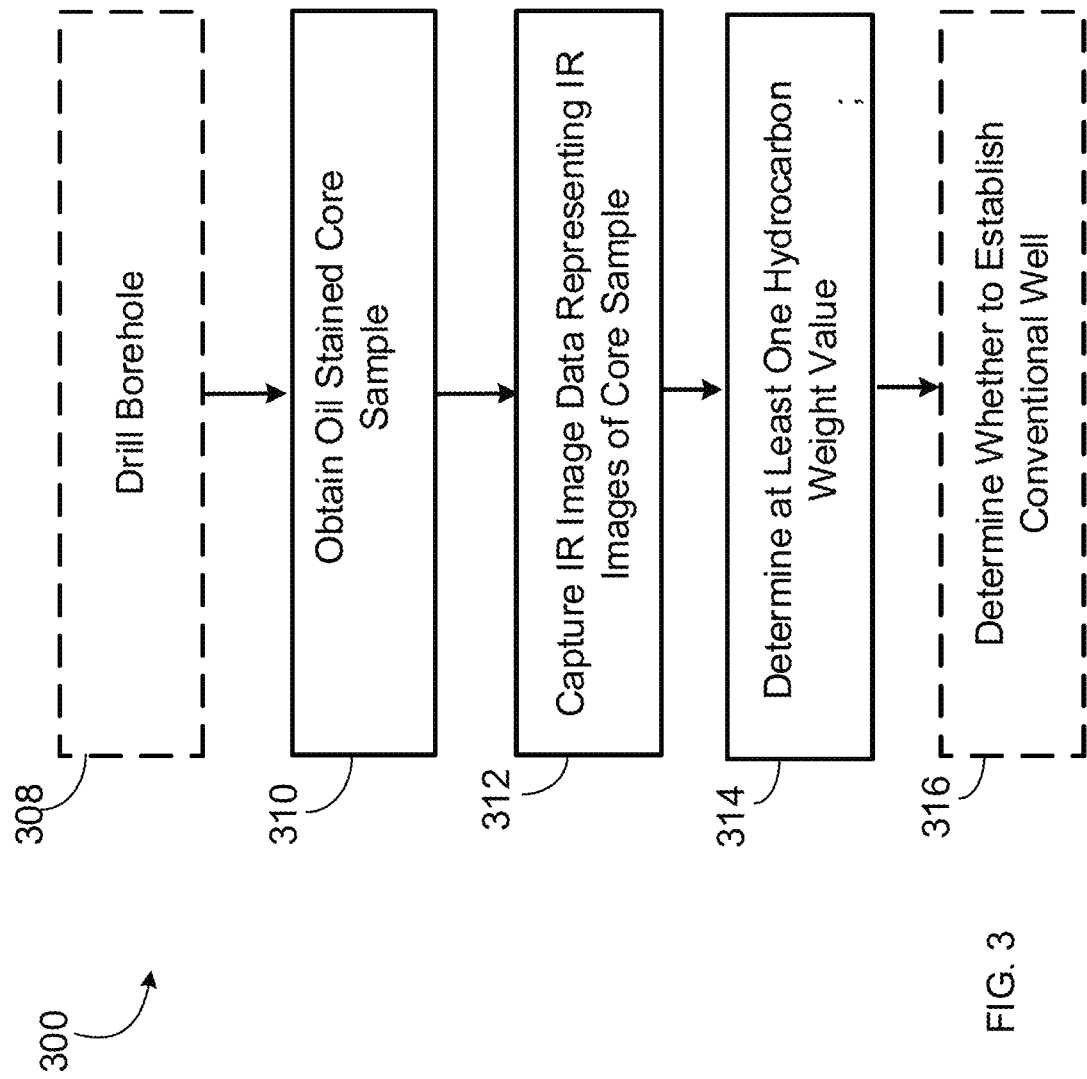
FIG. 3 is flowchart illustrating an example method for evaluating hydrocarbon properties.

FIG. 3 is flowchart illustrating an example method 300 for evaluating hydrocarbon properties. In some implementations, the system 200 discussed previously with reference to FIG. 2 performs all or portions of the method 300. The method 200 includes obtaining an oil stained core sample (block 310), capturing IR image data representing IR images of the core sample (block 312), and determining at least one hydrocarbon weight value (block 314). In some implementations, the method 300 includes drilling a borehole (block 308). In some implementations, the method 300 includes determining whether to drill a conventional well (block 316).

At block 308, a portable drilling system (for example, the drilling system 260 discussed previously with reference to FIG. 2) is used to drill a borehole. The borehole can be relatively smaller than a conventional well. For example, the borehole can have a depth of 3000 m. The borehole can be at or near a location of a planned location for establishing a conventional well.

At block 310, one or more oil stained core samples are obtained from the drilled borehole.

At block 312, a plurality of IR cameras are used to capture image data representing a plurality of IR images of the one or more oil stained core samples. As indicated previously, in some implementations, each of the IR cameras is sensitive to a different IR wavelength band than the other IR cameras.

At block 314, one or more API gravity values of the oil of each of the one or more oil stained core samples is determined based on the IR image data. In some implementations, the intensity values across the wavelength bands represented by the IR image data is compared with pre-defined probability density functions to determine the probability of several API values for the oil stained core sample.

At block 316, it is determined whether or not to establish a conventional well based on the determined one or more API gravity values. In some implementations, if it is determined to establish a conventional well, the determined one or more API gravity values are used to determine one or more methods for enhancing recovery (for example, injecting a substance, such as steam or carbon dioxide, into the well to increase pressure and reduce the viscosity of the oil).

Figure 4:
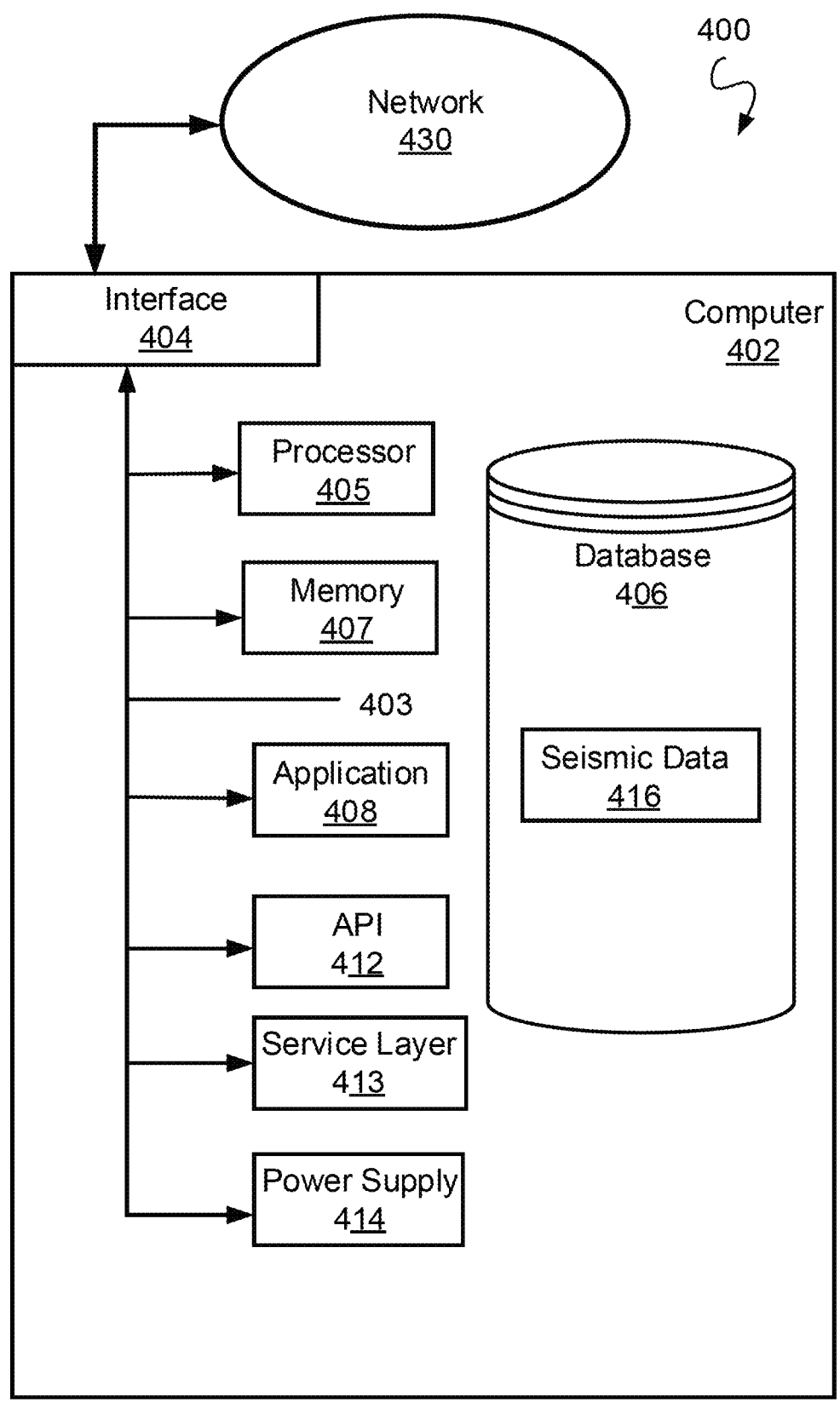
FIG. 4 is a block diagram illustrating an example computer system used to provide computational functionalities associated with described algorithms, methods, functions, processes, flows, and procedures as described in the present disclosure, according to some implementations of the present disclosure.

FIG. 4 is a block diagram of an example computer system 400 used to provide computational functionalities associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a high level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both), over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the hardware of the interface can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data (for example, seismic data 416) for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality.

While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of implementations of these systems and methods have been described. Nevertheless, it will be understood that various modifications may be made without departing from the spirit and scope of this disclosure. Accordingly, other implementations are within the scope of the following claims.

What is claimed is:

1. A system for evaluating hydrocarbon properties, comprising:
    a drilling machine configured to drill a borehole;
    a plurality of infrared cameras configured to capture infrared image data representing a plurality of infrared images of at least one core sample extracted from the borehole, wherein the plurality of IR cameras are configured to capture infrared data at wavelengths between 1,400 nm and 15,000 nm;
    a computer-readable memory comprising computer-executable instructions; and
        at least one processor configured to execute the computer-executable instructions, wherein when the at least one processor is executing the computer-executable instructions, the at least one processor is configured to carry out operations comprising:
            receiving the infrared image data captured by the plurality of infrared cameras;
            determining, based on the infrared image data, at least one hydrocarbon weight value of the at least one core sample.

2. The system of claim 1, wherein determining at least one hydrocarbon weight property comprises executing at least one machine learning model trained to predict an American Petroleum Institute (API) gravity value based on infrared intensity values of the infrared image data.

3. The system of claim 1, wherein the plurality of IR cameras comprises:
    at least one short-wavelength IR camera configured to capture infrared image data at wavelengths between 1400 nanometers (nm) and 3000 nm;
    at least one mid-wavelength IR camera configured to capture infrared image data at wavelengths between 3000 nm and 8000 nm; and
    at least one long-wavelength IR camera configured to capture infrared image data at wavelengths between 8000 nm and 15000 nm.

4. The system of claim 1, wherein the drilling machine comprises a portable drilling machine configured to drill a maximum borehole depth of 3000 meters (m).

5. The system of claim 1, wherein determining at least one hydrocarbon weight is further based on a plurality of predetermined probability density functions defined by a plurality of measured intensity values.

6. The system of claim 1, wherein determining at least one hydrocarbon weight property comprises executing at least one machine learning model trained to predict a probability of a plurality of API gravity values based on infrared intensity values of the infrared image data.

7. A method for evaluating hydrocarbon properties, comprising:
    drilling, using a drilling machine, a borehole;
    capturing, using a plurality of infrared cameras, infrared image data representing a plurality of infrared images of at least one core sample extracted from the borehole wherein the plurality of IR cameras are configured to capture infrared data at wavelengths between 1,400 nm and 15,000 nm;
    receiving, by at least one processor, the infrared image data captured by the plurality of infrared cameras;
    determining, by the at least one processor and based on the infrared image data, at least one hydrocarbon weight value of the at least one core sample.

8. The method of claim 7, wherein determining at least one hydrocarbon weight property comprises executing at least one machine learning model trained to predict an American Petroleum Institute (API) gravity value based on infrared intensity values of the infrared image data.

9. The method of claim 7, wherein the plurality of IR cameras comprises:
    at least one short-wavelength IR camera configured to capture infrared image data at wavelengths between 1400 nanometers (nm) and 3000 nm;
    at least one mid-wavelength IR camera configured to capture infrared image data at wavelengths between 3000 nm and 8000 nm; and
    at least one long-wavelength IR camera configured to capture infrared image data at wavelengths between 8000 nm and 15000 nm.

10. The method of claim 7, wherein determining at least one hydrocarbon weight is further based on a plurality of predetermined probability density functions defined by a plurality of measured intensity values.

11. The method of claim 7, wherein determining at least one hydrocarbon weight property comprises executing at least one machine learning model trained to predict a probability of a plurality of API gravity values based on infrared intensity values of the infrared image data.

12. A non-transitory computer storage medium encoded with computer program instructions that when executed by one or more computers cause the one or more computers to perform operations comprising:

receiving, by at least one processor, infrared image data captured by a plurality of infrared cameras and representing a plurality of infrared images of at least one core sample extracted from a borehole, wherein the plurality of IR cameras are configured to capture infrared data at wavelengths between 1,400 nm and 15,000 nm;

determining, by the at least one processor and based on the infrared image data, at least one hydrocarbon weight value of the at least one core sample.

13. The non-transitory computer storage medium of claim 12, wherein determining at least one hydrocarbon weight property comprises executing at least one machine learning model trained to predict an American Petroleum Institute (API) gravity value based on infrared intensity values of the infrared image data.

14. The non-transitory computer storage medium of claim 12, wherein determining at least one hydrocarbon weight is further based on a plurality of predetermined probability density functions defined by a plurality of measured intensity values.

15. The non-transitory computer storage medium of claim 12, wherein determining at least one hydrocarbon weight property comprises executing at least one machine learning model trained to predict a probability of a plurality of API gravity values based on infrared intensity values of the infrared image data.

* * * * *